United States Patent [19]

Haveland

[11] Patent Number: 5,601,714
[45] Date of Patent: Feb. 11, 1997

[54] DEVICE FOR FILTRATION AND COLLECTION OF BLOOD

[75] Inventor: Sverre M. Haveland, Frederiksberg, Denmark

[73] Assignee: Polystan Holding A/S, Vaerlose, Denmark

[21] Appl. No.: 268,491

[22] Filed: Jun. 30, 1994

[51] Int. Cl.⁶ .............. B01D 29/00; B01D 29/13; B01D 29/50; A61M 1/00
[52] U.S. Cl. ............. 210/436; 210/435; 210/444; 210/451; 210/454; 210/472; 210/483; 210/488; 210/489; 210/496; 210/497.01; 210/497.3; 210/499; 422/44; 422/45; 604/317; 604/324
[58] Field of Search ............... 210/435, 436, 210/444, 454, 455, 472, 483, 488, 489, 496, 497.01, 451, 497.3, 499; 422/44, 45; 604/317, 321, 322, 324, 403

[56] References Cited

U.S. PATENT DOCUMENTS 5,039,430  8/1991  Corey, Jr. ................. 210/436
5,127,900  7/1992  Schickling et al. ......... 604/4
5,411,705  5/1995  Thor et al. ................. 210/436

FOREIGN PATENT DOCUMENTS 0190020  3/1991  European Pat. Off. .

*Primary Examiner*—John Kim
*Attorney, Agent, or Firm*—Kerkam, Stowell, Kondracki & Clarke; Dennis P. Clarke

[57] ABSTRACT

A disposable device for filtration and collection of blood during a surgical operation, which device comprises a housing with a cup-shaped portion, in which a wall section is forming a ledge in the reservoir inside the housing. A first self-supporting filtration element for venuous blood is upstanding from the ledge, and a second filtration element for cardiotomy blood is suspended from the cover, the two elements being arranged side by side in a parallel relationship. The filter elements have an elongate, oval cross-section.

5 Claims, 5 Drawing Sheets

DEVICE FOR FILTRATION AND COLLECTION OF BLOOD

SUMMARY OF THE INVENTION

The present invention relates to a device for filtration and collection of blood from two different sources during a surgical procedure, said device comprising a housing made of a rigid material and having a cover, side walls, and a bottom wall;

a reservoir defined within the device for collecting filtered blood and provided with an outlet in the bottom wall;

a first blood filter element inside the housing comprising in series a layer of porous defoaming material and a screen filter;

a first blood inlet in said housing, which inlet is connected with means providing a first blood path in the device through said first inlet, said first blood filter element, said reservoir, and said blood outlet;

a second blood filter element comprising in series a layer of porous defoaming material, a depth filter and a stocking;

at least one second blood inlet in the cover, which inlet is connected with means providing a second blood path in the device through said second inlet, said second blood filter element, said reservoir, and said blood outlet; and a gas vent in said cover of the housing in communication with said reservoir.

BACKGROUND OF THE INVENTION

Devices of this type are used in surgical procedures referred to in the art as cardiopulmonary bypass operations. During such procedure the normal function of the patient's heart and lungs is suspended, and the function of these organs is replaced by artificial blood handling and treating units in a life-sustaining extracorporeal blood flow circuit. In these procedures the main body of the patient's blood is typically withdrawn from the patient through a cannula inserted into the right atrium and passed through a filtered reservoir, a blood pump, a blood oxygenator, and an arterial blood filter before being returned to the patient through a cannula inserted into the aorta. The main blood stream is in accordance with typical practice combined with blood collected from the surgical field, which blood is gathered in one or more cardiac vacuum suckers and after defoaming and depth filtering collected in the reservoir, which is common for the two blood paths before being extracted through the blood outlet through an extracorporeal blood pump. A device Of this type is disclosed in EP-B-0 190 020.

For surgical Operations of this kind it is important to reduce the priming volume of the device, which is normally done by adapting the size of the device to the size of the patient. The known device comprises a number of elements arranged inside the filter for supporting the filter and the defoaming material and for providing the flow paths for the two blood streams within the filter. This is especially disadvantageous if the filter is to be made in a number of different sizes because of the large number of parts.

It is an object of the invention to provide a device in which the filter element does not contain internal support or flow control elements and in which an increased filter area is obtainable for a predetermined priming volume.

The device according to the invention is characteristic in that the housing above the bottom comprises a wall forming a ledge in said reservoir and defining a bottom wall in a portion of the reservoir with enlarged cross-section;

that said first filter at the lower end is connected with said ledge, in the bottom wall of which said first inlet is placed;

that said second filter is mounted in the cover and is extending downwards towards said ledge, with which it is in contact, that said first filter is extending upwards from said ledge and is self-supporting; and that said first and second filters are arranged side by side in parallel relationship.

The arrangement of the filters side by side results in a compact construction of the device and a short path of the filtered blood from the filter to the reservoir. The filters may have a shape which increases the filter area compared with filters of circular cross-section.

Preferred embodiments of the invention are defined in the subclaims. The filters preferably have an oval cross-section and a rounded profile. This shape is suited for making the filters self-supporting and is providing a comparatively large filter area in relation to the volume inside the filter. The filters are preferably bonded into oval recesses in the cover and ledge of the housing forming a rigid fastening of thee filters. In order to ensure a smooth flow of blood into the reservoir, the ledge has a gradient towards an inclined part of the reservoir. This arrangement prevents the forming of bubbles in the filtered blood. The filters are made from blanks which are welded along the edges before being turned inside out. The welding seam contributes to the self-supporting capacity of the filters.

The invention will be described in detail with reference to a preferred embodiment thereof which is a disposable blood treatment and collection device shown in the drawing and for use in an extracorporeal blood flow circuit.

DESCRIPTION OF THE PREFERRED EMBODIMENTS

Figure 1:
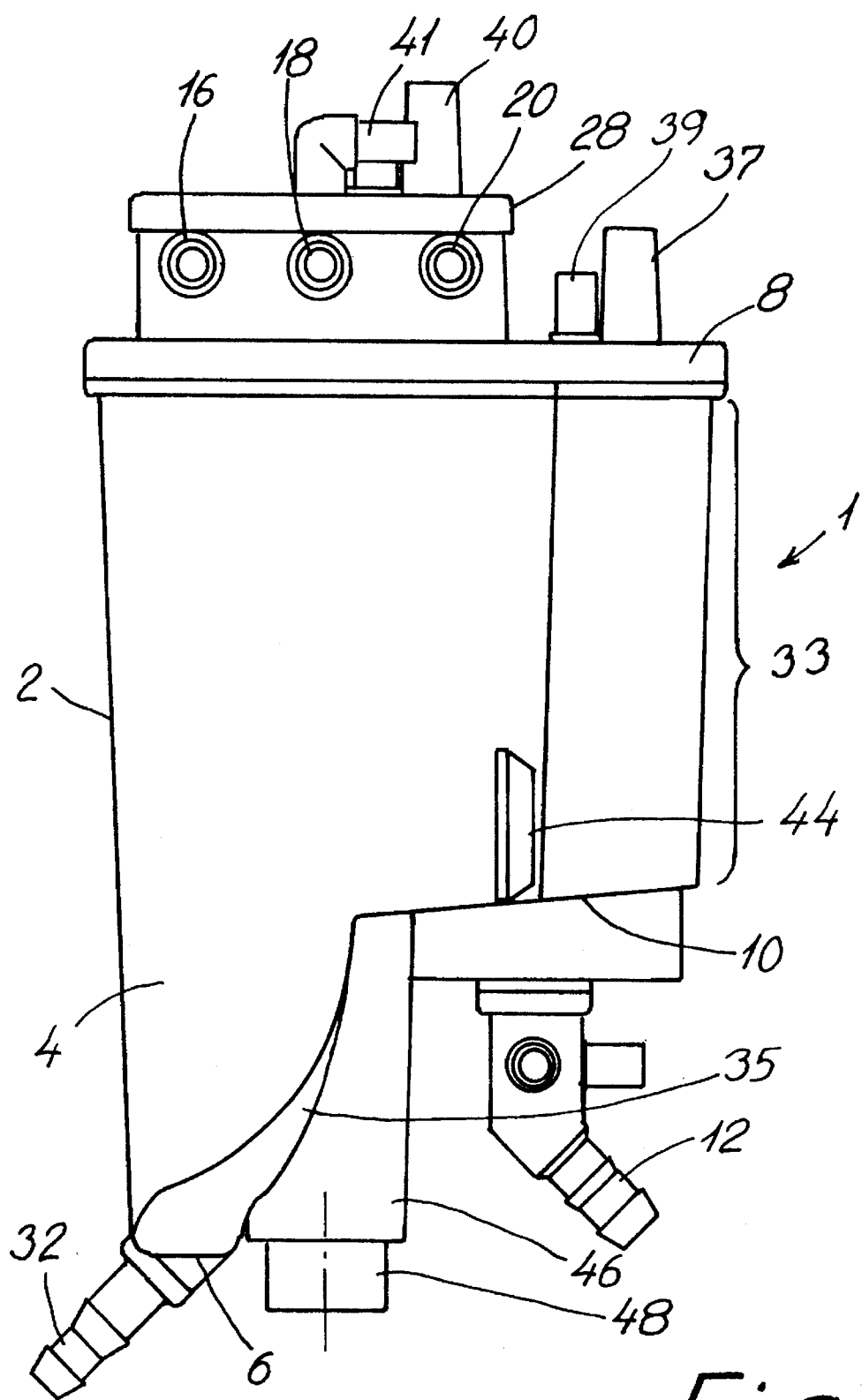
FIG. 1 is a side view of an extracorporeal blood treatment and collection device according to the invention.
Figure 2:
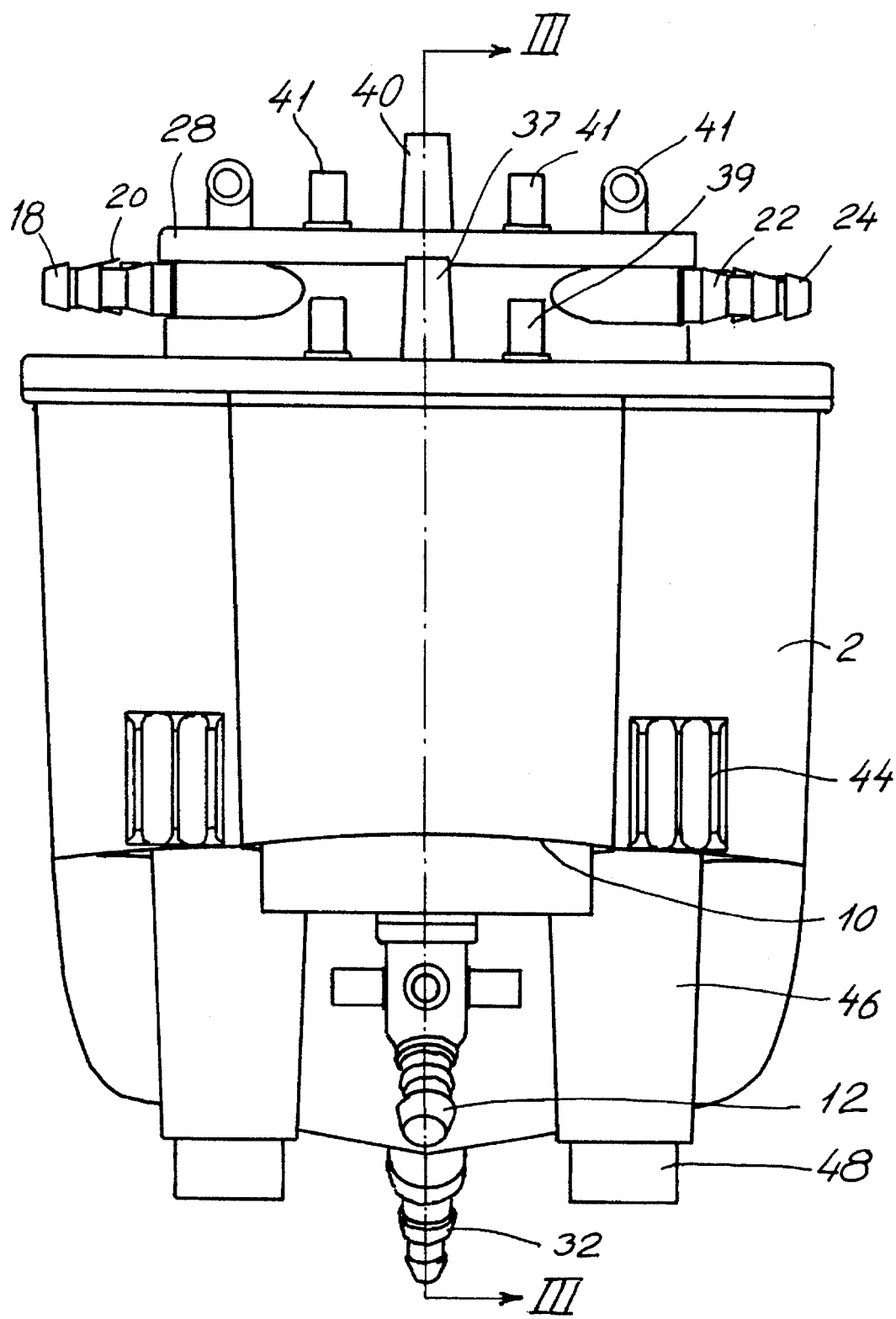
FIG. 2 is a front view of the device according to FIG. 1.
Figure 3:
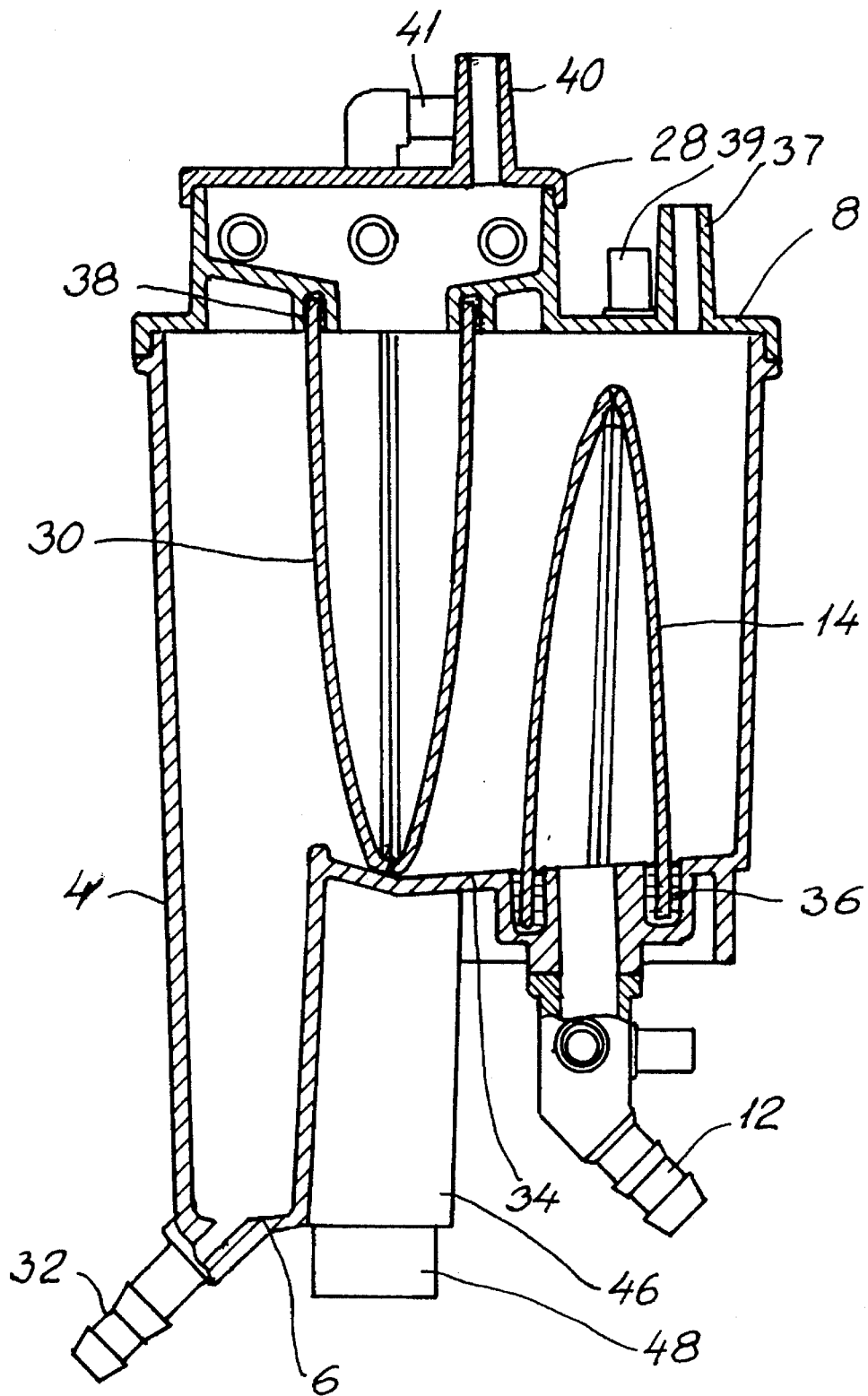
FIGS. 3 and 5 are sectional view along the line III—III in FIG. 2.
Figure 4A:
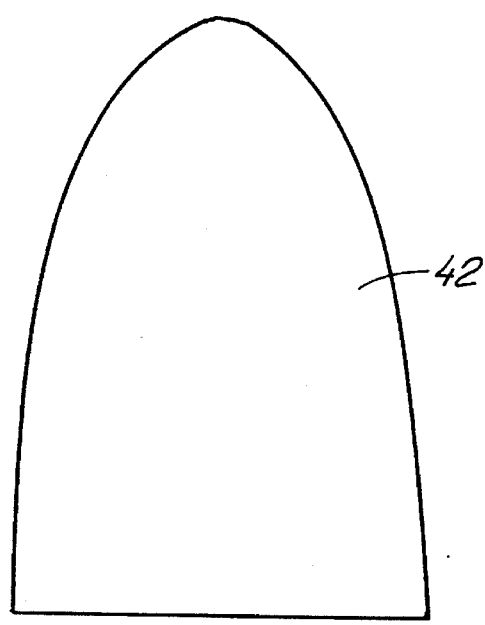
FIGS. 4a–d are front, side, sectional, and perspective views of a filter element for the device according to the invention.
Figure 4B:
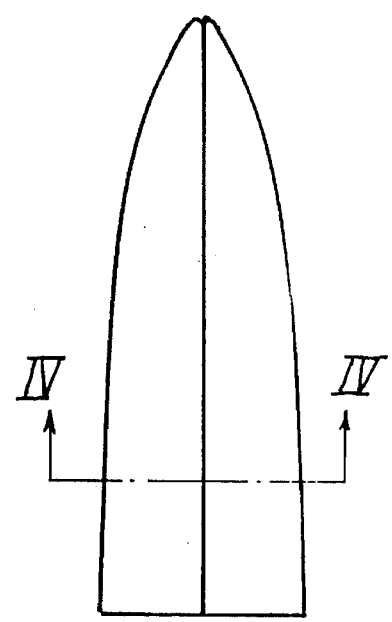
Figure 4D:
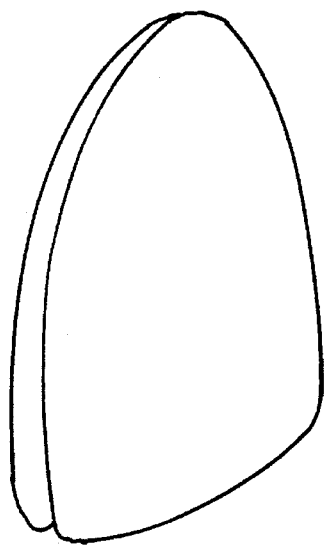
Figure 4C:
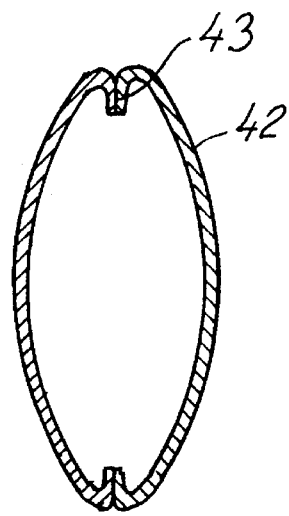
Figure 5:
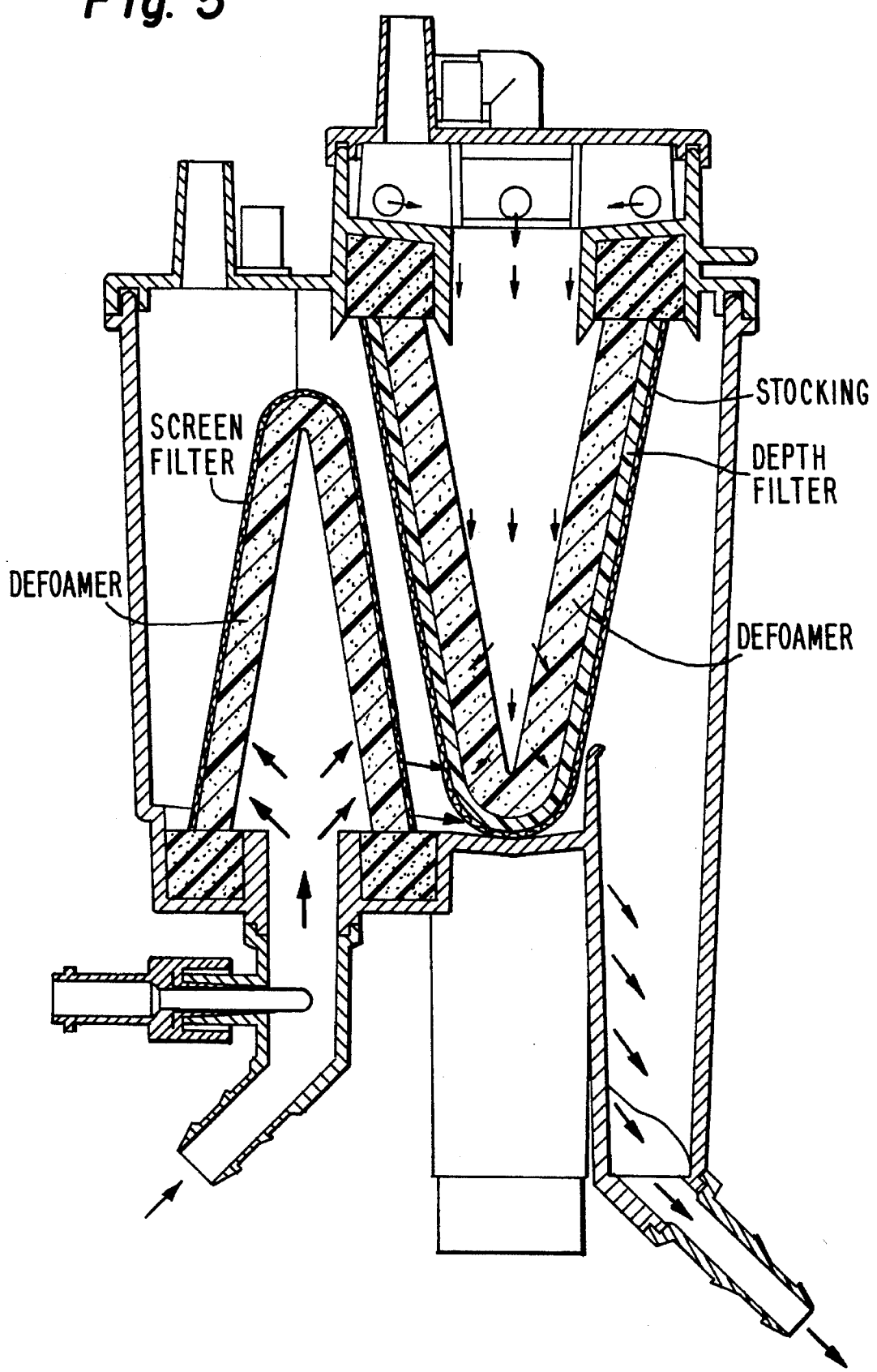

A disposable blood filtration and collection device of the invention is Shown in FIGS. 1 to 3. The device comprises a housing 2 having side walls 4, a bottom wall 6, and a cover 8. The device further comprises a wall 10 forming a ledge inside the housing, which ledge is the bottom wall in a portion of the housing with an enlarged cross-section. The device has a blood inlet 12 in communication with the inner space of a first blood treatment element 14 and a number of parallel blood inlets 16,18,20,22,24 placed in a top cap 28 on the cover 8 and in communication with the inner space of a second blood filter element 30. In normal operation of the device 1, one or more lines of tubing conducting cardiotomy suction blood are connected to one or more of the inlets 16,18,20,22,24, and a line carrying the venous blood return stream is connected to the inlet 12. Accordingly, as shown by arrows in FIG. 3, the cardiotomy blood passes through the element 30 and the venous return blood passes through and is filtered by the element 14. The filtered venuous blood is combined with the filtered cardiotomy blood from the second element 30, and the combined streams of blood are collected in a reservoir defined generally by the side walls 4 and the bottom wall 6 of the housing. The combined treated cardiotomy and venuous blood is withdrawn from the device through a treated blood outlet 32. Tubing organizers 44 are elements for fixing the various tubes required for connecting and/or interconnecting when using the blood filter. Legs 46 with feet 48 fixed thereon support the filter during use. The feet 48 may be glued to the upper part of an oxygenator (not shown) when the filter is used in conjunction with such a device. The upper part of the oxygenator may be provided with mating indentations for alignment. The feet 48, as well as legs 46, are provided with bores (not shown, extending vertically in the whole length of feet 48 and legs 46 as viewed in FIGS. 1—3). The apparatus according to the invention may conveniently be supported during use by placing it on a support which has a post or hook which engages in one or both of these bores.

The housing is made preferably by injection moulding from a preferably transparent plastic material. In the preferred embodiment shown in the figures, the housing is formed by bonding a disc-shaped cover 8 to a generally cup-shaped body portion 33. The cover 8 may include a gas vent 37 and additional ports 39 and in the top cap 28 a gas vent 40 and a number of additional ports 41 for introduction of blood or other fluids upstream or downstream of the filter element 30. The venous blood inlet 12 and the treated blood outlet 32 may be in a single-piece construction with the housing, or, as shown in the preferred embodiment, separate components sealed and bonded to the wall of the housing.

As shown in FIG. 3, the blood filter elements 14 and 30 are arranged side by side in a parallel relationship. The blood filter elements are self-supporting, the first element 14 is upstanding from the ledge 34, and the second element 30 is connected to and hanging downward from the cover 8. The length of the second element 30 is such that the lower end of the element is in contact with the ledge. Blood which has been filtered by the second element 30 flows along the surface of the element and passes smoothly to the upper surface of the ledge 34, which has a gradient towards an inclined part 35 of the side wall 4. With this arrangement the formation of droplets falling into a free surface of the blood collected in the reservoir is avoided.

The blood filter element 14 is inserted into an oval groove 36 in the ledge, after which it is sealed by means of a polyurethane potting compound. The second filter element 30 is inserted in a similar groove 38 in the cover 8 and similarly sealed with a potting compound.

FIGS. 4 a–d show in detail a filter element. The element comprises two blanks 42 welded together along the edges to form a bag-like assembly, which afterwards is turned inside out. The welding seam 43 forms a stiffening formation making the element self-supporting and holding the sides of the element apart and providing the element with an oval cross-section. The blood filter element 12 comprises an inner layer of a porous defoaming material, preferably a reticulated polyurethane foam treated with an antifoam compound, such as a silicone antifoam agent, and an outer layer of, for example, a thin screen filter of uniform pore size, preferably a woven nylon or polyester screen having a pore size between 50 and 200 microns, preferably about 175 microns. The blood filter element 30 comprises an inner layer of porous defoaming material followed by a layer of a non-wowen depth filter material, preferably a fibrous polyester depth filter material having a mean pore size of 20 to 50 microns, preferably about 40 microns, and an outside stocking.

The blood filtration device may also include fittings for suspending the device on an oxygenator/heat exchanger or alternatively onto a hanger from a heart-lung machine (HLM). The cover, the top cap, the body portion, and the inlet and outlet fittings are preferably made by conventional methods from a clear plastic material, preferably a copolyester or polycarbonate.

I claim:

1. A device for filtration and collection of blood from two different sources during a surgical procedure, said device comprising:

a housing made of a rigid material and having a cover, side walls and a bottom wall;

a reservoir defined within the device for collecting filtered blood and provided with and a blood outlet in the bottom wall;

a first blood filter element inside the housing comprising in series a layer of porous defoaming material and a screen filter;

a first blood inlet in said housing, which inlet is connected with means providing a first blood path in the device through said first blood inlet, said first blood filter element, said reservoir and said blood outlet;

a second blood filter element comprising in series a layer of porous defoaming material, a depth filter and a stocking;

at least one second blood inlet in the cover, which inlet is connected with means providing a second blood path in the device through said second blood inlet, said second blood filter element, said reservoir and said blood outlet;

a gas vent in said cover of the housing in communication with said reservoir;

wherein the housing above the bottom wall comprises a wall forming a ledge in said reservoir and defining a bottom wall in a portion of the reservoir with enlarged cross-section;

said first blood filter element at the lower end thereof is connected with said ledge, in the bottom wall of which said first blood inlet is placed;

said second blood filter element is mounted in the cover and is extending downwards towards said ledge, with which it is in contact;

said first blood filter element is extending upwards from said ledge and is self-supporting; and said first and second blood filter elements are arranged side by side in parallel relationship.

2. A device according to claim 1, wherein the blood filter elements have an oval cross-section and a rounded profile.

3. A device according to claim 2, wherein the said first and second blood filter elements are bonded into an oval recess in the ledge and in the cover, respectively.

4. A device according to claim 1, wherein the wall forming the ledge has a gradient towards an inclining portion of the wall of the reservoir.

5. A device according to claim 1, wherein the blood filter elements are made from two blanks which are welded along the edges and turned inside out.

* * * * *